(12) United States Patent
Onda et al.

(10) Patent No.: US 9,613,419 B2
(45) Date of Patent: Apr. 4, 2017

(54) IMAGE GENERATING DEVICE AND IMAGE GENERATING METHOD

(71) Applicant: CANON KABUSHIKI KAISHA, Tokyo (JP)

(72) Inventors: Suguru Onda, Yokohama (JP); Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 42 days.

(21) Appl. No.: 14/712,252

(22) Filed: May 14, 2015

(65) Prior Publication Data

US 2015/0339822 A1 Nov. 26, 2015

(30) Foreign Application Priority Data

May 22, 2014 (JP) ................................ 2014-106233

(51) Int. Cl.
| | |
|---|---|
| G06K 9/00 | (2006.01) |
| G06T 7/00 | (2017.01) |
| G06T 1/00 | (2006.01) |
| G06T 3/00 | (2006.01) |
| A61B 3/00 | (2006.01) |

(52) U.S. Cl.
CPC .......... *G06T 7/0028* (2013.01); *A61B 3/0025* (2013.01); *G06T 1/0007* (2013.01); *G06T 3/0068* (2013.01); *G06T 3/0075* (2013.01); *G06T 7/0012* (2013.01); *G06T 7/0026* (2013.01); *G06T 2200/32* (2013.01); *G06T 2207/10004* (2013.01); *G06T 2207/10056* (2013.01); *G06T 2207/10152* (2013.01);
(Continued)

(58) Field of Classification Search
CPC ... G06T 7/0028; G06T 1/0007; G06T 3/0075; G06T 7/0012; G06T 2200/32; G06T 2207/10004; G06T 2207/20221; G06T 3/0068; G06T 7/0026; G06T 2207/30041; G06T 2207/10056; G06T 2207/10152; A61B 3/0025
USPC ........................................................ 382/128
See application file for complete search history.

(56) References Cited

U.S. PATENT DOCUMENTS

| | | | |
|---|---|---|---|
| 8,235,528 | B2 | 8/2012 | Mukai et al. |
| 8,851,673 | B2 | 10/2014 | Hirose |

(Continued)

FOREIGN PATENT DOCUMENTS

| | | |
|---|---|---|
| JP | 2010-259543 | 11/2010 |
| JP | 2013-169332 | 9/2013 |

OTHER PUBLICATIONS

European Search Report issued in counterpart European Patent Application No. 15168324.0 mailed Oct. 26, 2015.

*Primary Examiner* — Gregory F Cunningham
(74) *Attorney, Agent, or Firm* — Fitzpatrick, Cella, Harper & Scinto (57) ABSTRACT

To enable accurate stitching of images in generating a panoramic image by performing position adjustment of an image group with few characters, an image processing device includes: a calculation unit that calculates degrees of correlation between a plurality of images; a second calculation unit that calculates character amounts of a plurality of images; and an order determination unit that determines an order of performing position adjustment of the plurality of images for generating a panoramic image generated by stitching the plurality of images based on calculation results of the calculation unit and the second calculation unit.

21 Claims, 9 Drawing Sheets

(52) U.S. Cl.
CPC .............. *G06T 2207/20221* (2013.01); *G06T 2207/30041* (2013.01)

(56) References Cited

U.S. PATENT DOCUMENTS

| | | | |
|---|---|---|---|
| 2007/0237423 A1* | 10/2007 | Tico | G06T 3/4038 382/284 |
| 2010/0277692 A1 | 11/2010 | Mukai et al. | |
| 2011/0058715 A1* | 3/2011 | Doering | G06T 3/4038 382/128 |
| 2013/0215384 A1 | 8/2013 | Hirose | |
| 2014/0347627 A1 | 11/2014 | Imamura | |

\* cited by examiner

IMAGE GENERATING DEVICE AND IMAGE GENERATING METHOD

BACKGROUND OF THE INVENTION

Field of the Invention

The present invention relates to an image generating device and an image generating method.

Description of the Related Art

Examination of fundus is widely performed for early diagnosis of illnesses that are leading causes of lifestyle related diseases and blindness. For example, there is a scanning laser ophthalmoscope (SLO) that is an ophthalmic device using the principle of a confocal laser scanning microscope. The SLO is a device that performs raster scan of a fundus with a laser, which is measuring light, to obtain a planar image from the intensity of the return light, at high resolution and high speed.

In recent years, an adaptive optics SLO (AO-SLO) including an adaptive optics system is developed, in which a wavefront sensor measures the aberration of an examined eye in real time, and a wavefront correction device corrects the aberration of the measuring light or the return light generated in the examined eye. A planar image with a high horizontal resolution (hereinafter, may be called AO-SLO image) can be acquired.

When a planar image with a high horizontal resolution is acquired, the imaging range to be photographed at a time, i.e., field angle, is narrowed down due to a problem of optical aberration of the device or an increase in the imaging time. Therefore, the fundus needs to be imaged at a plurality of positions in a relatively wide range to obtain information necessary for diagnosis and examination. In some cases, a local region of an eye of the subject is imaged for a plurality of times in a predetermined range to figure out the entire eye, even if the images are not high-magnification images.

However, in these cases, the relationship between the plurality of obtained photographed images needs to be figured out even if the area necessary for diagnosis and examination is imaged. More specifically, the positional relationship between the plurality of photographed images needs to be clarified to stitch the images according to the positions of the images to thereby generate one high-definition panoramic image.

To solve the problem, Japanese Patent Application Laid-open No. 2010-259543 proposes a combined device with a combination of an SLO device with a wide field angle and a high-resolution SLO device with a small field angle, thereby making an attempt to solve the problem. When a desired position of an examined eye is imaged, a fixation lamp for fixating the examined eye is often used. In an invention disclosed in Japanese Patent Application Laid-Open No. 2013-169332, the displayed position of the fixation lamp is adjusted according to the diopter scale of the examined eye to acquire a planar image of a desired position of the fundus.

Performing position adjustment of a plurality of images to create a panorama is a general method. However, when the characters of a high-definition image of fundus with a small field angle are significantly small structural objects, such as photoreceptor cells and capillary vessels, the characters may not be resolved in a wide-angle image. In this case, combining of a small-angle image with few characters and a wide-angle image is not easy, and there is a case in which the images do not match in the method disclosed in Japanese Patent Application Laid-Open No. 2010-259543. Even between small-angle images, when position adjustment of an image with few characters is performed first, there may be a case in which an image for which the position adjustment will be performed next does not match. Unmatched images tend to be prominent when there is a disorder in the eye to be observed, such as when the signal intensity is weak due to cataract or when a normal anatomical structure disappears due to other diseases.

Because of the problems, a plurality of small field angles needs to be imaged to include an overlapped area (overlap), in which both images include at least character points that are some kind of structural objects. For example, a region of fundus to be observed is sequentially imaged in a tile shape or according to the shape of a structural object, such as a blood vessel and a lesion (edema or bleeding) that serves as a character. However, even a little involuntary eye movement moves the examined eye, and the expected location is shifted. An image without an area overlapping with the images taken so far or an image without a character point in the previous image may be taken. In this case, if images with a small field angle are sequentially stitched in the order of imaging, an image in which the position cannot be determined may be generated depending on the order of stitching.

A false detection of the position adjustment can be suppressed if the imaging position can be recognized from imaging conditions. However, when a fixation index is used to adjust the imaging position as disclosed in Japanese Patent Application Laid-Open No. 2013-169332, there is usually involuntary eye movement of the examined eye, and particularly, it is significantly difficult to accurately specify the imaging position when the visual fixation of the affected eye is poor or when the tested person or animal cannot see the fixation lamp.

SUMMARY OF THE INVENTION

The present invention has been made in view of the circumstances, and an object of the present invention is to provide an image generating device and an image generating method that can reduce failures in stitching images than in the past.

To solve the problems, the present invention provides an image generating device including:

a calculation unit that calculates degrees of correlation between a plurality of images; and an order determination unit that determines an order of performing position adjustment of the plurality of images for generating a panoramic image generated by stitching the plurality of images based on calculation results of the calculation unit.

According to the present invention, failures in stitching can be automatically reduced.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

The following embodiment is not intended to limit the present invention regarding the claims, and combinations of features described in the present embodiment may not be all essential to solve the problems of the present invention.

The present embodiment describes a process, in which an adaptive optics SLO takes images of a retina in a plane surface to acquire a plurality of images (planar images of retina), and then image position adjustment of the images is performed to generate a panoramic image. The planar images of retina here denote front images obtained when an examined eye is imaged by a fundus camera from the front side.

Specifically, character amounts of the images and degrees of correlation between the plurality of images are calculated, and the sizes of the character amounts and the sizes of the degrees of correlation are taken into account to determine the order of position adjustment. The determined order is used to sequentially perform position adjustment and stitching of the images to generate the panoramic image. Using such a step can accurately stitch a small-angle image group with few characters as in fundus images even if accurate position information of images cannot be recognized and can reduce the number of stitching failed images.

<Configuration of Image Generating Device>

Figure 1:
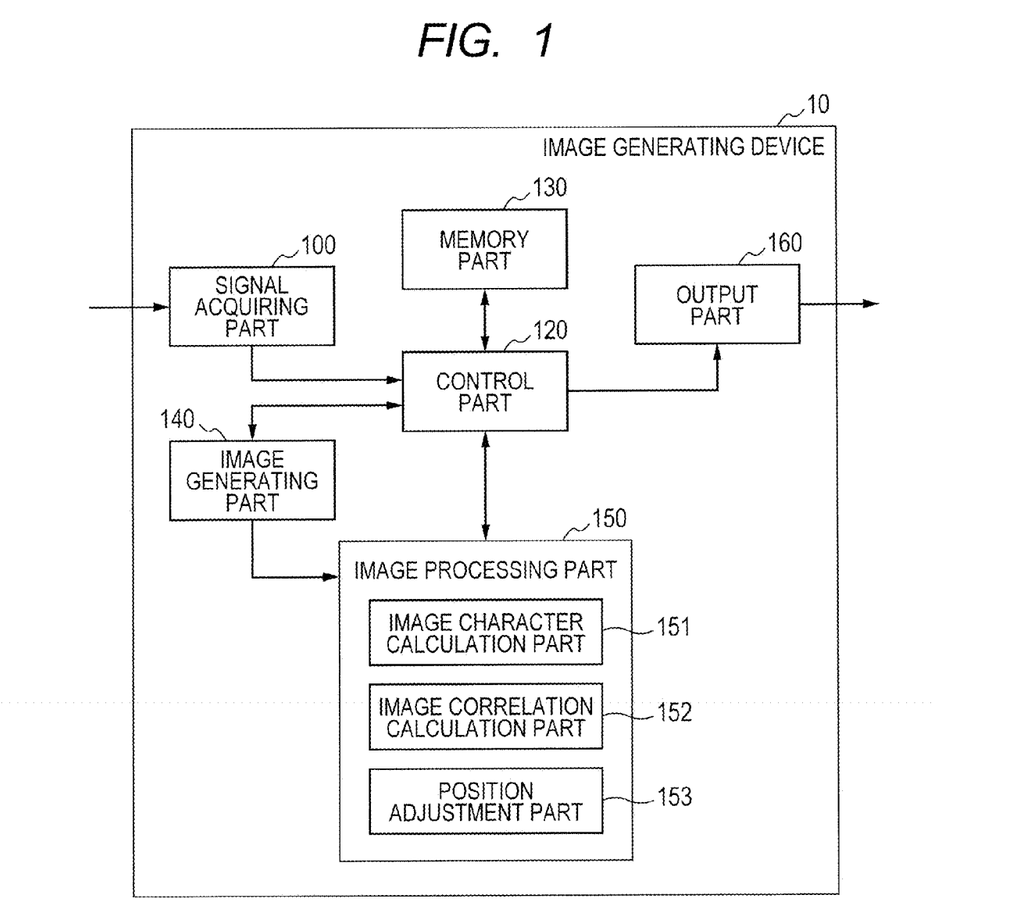
FIG. 1 is a block diagram illustrating a functional configuration of an image generating device according to the present invention.
Figure 2:
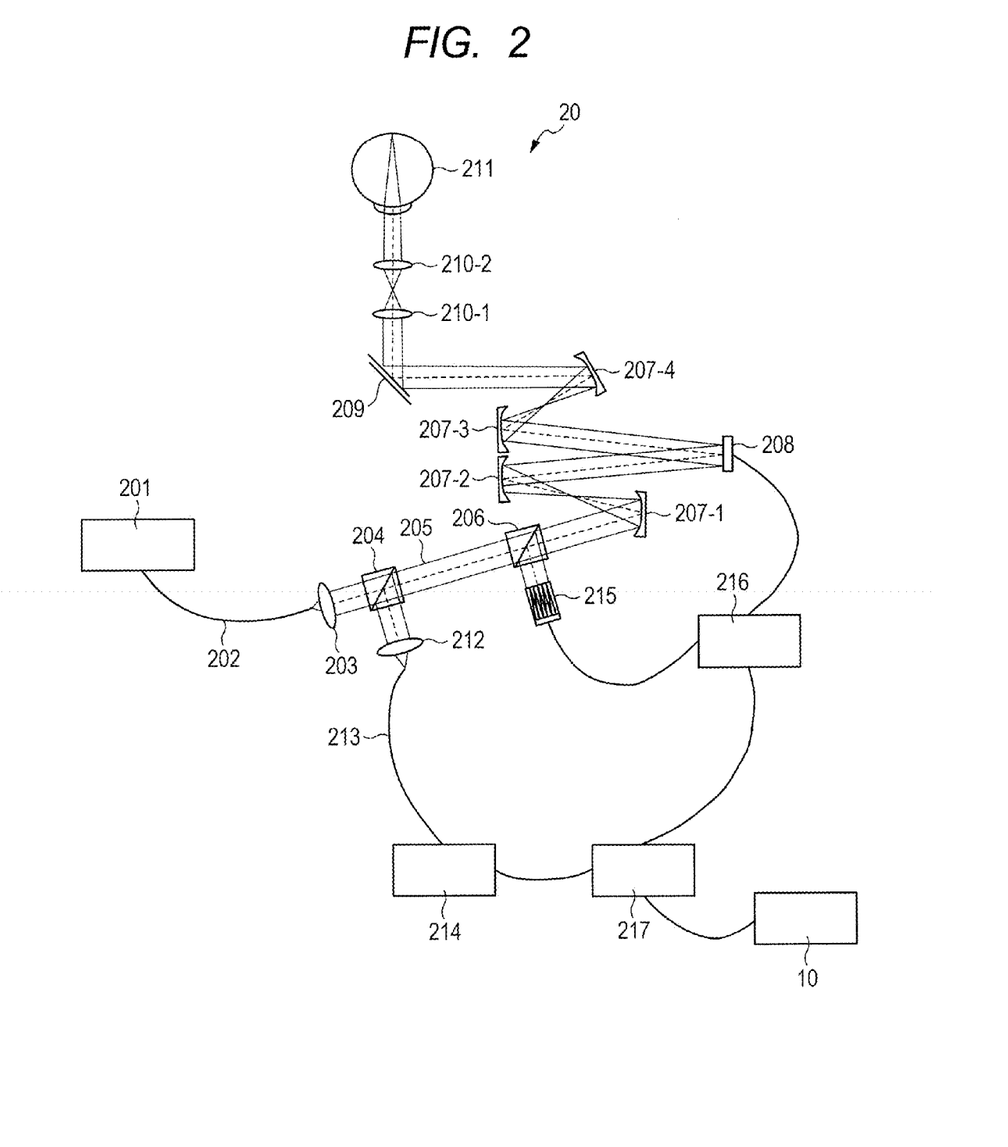
FIG. 2 is a schematic diagram illustrating a configuration of an adaptive optics SLO according to the present invention.

FIG. 1 illustrates a functional configuration of an image generating device 10 according to the present embodiment, and the image generating device 10 is connected to an adaptive optics SLO device of FIG. 2. In FIG. 1, a signal acquiring part 100 acquires reflected signals from a retina and other information necessary for image generation from the adaptive optics SLO device. The acquired information is stored in a memory part 130 through a control part 120. An image generating part 140 uses the acquired information to form, images from the reflected signals. An image character calculation part 151 uses the generated images to calculate character amounts of the images, and an image correlation calculation part 152 calculates degrees of correlation between the images. A position adjustment part 153 uses the arithmetic results to determine an order of position adjustment. The position adjustment part 153 sequentially performs position adjustment and image stitching according to the determined order. In this way, an image processing part 150 performs the operation to generate a panoramic image. An output part 160 outputs the generated image to a monitor not illustrated.

A configuration of the SLO image pickup device including an adaptive optics system, will be described with reference to FIG. 2. An SLD light source (Super Luminescent Diode) is used as a light source 201, Although a common light source is used, for imaging and wavefront measurement in the present embodiment, separate light sources may be used, and waves may be multiplexed in the middle. Light emitted from the light source 201 passes through a single-mode optical fiber 202, and a collimator 203 emits parallel measuring light 205. The emitted measuring light 205 transmits through a light dividing part 204 made of a beam splitter and is guided to the adaptive optics system.

The adaptive optics system includes a light dividing part 206, a wave front sensor 215, a wavefront correction device 208 and reflection mirrors 207-1 to 4 for guiding the light to these. The reflection mirrors 207-1 to 4 are installed so that at least the pupil of the eye is optically conjugated to the wavefront sensor 215 and the wavefront correction device 208. A beam splitter is used as the light dividing part 206 in the present embodiment. A space phase modulator using a liquid crystal element is used as the wavefront correction device 208 in the present embodiment. A variable shape mirror may be used as the wavefront correction device.

A scanning optical system 209 one-dimensionally or two-dimensionally scans the fundus with the light passed through the adaptive optics system. Two galvano scanners for main-scanning (horizontal direction of fundus) and for sub-scanning (vertical direction of fundus) are used as the scanning optical system 209 in the present embodiment. For faster imaging, a resonant scanner may be used on the main-scan side of the scanning optical system 209. The measuring light 205 used for scanning by the scanning optical system 209 is emitted to an eye 211 through eyepieces 210-1 and 210-2.

The measuring light 205 emitted to the eye 211 is reflected or scattered by the fundus. The positions of the eyepieces 210-1 and 210-2 can be adjusted to perform optimal emission according to the diopter scale of the eye 211, Although lenses are used for the eyepiece parts here, the eyepiece parts may be spherical mirrors. The reflected and scattered light (return light) reflected or scattered from the retina of the eye 211 advances in the opposite direction, through the same path as when the light has entered. The light dividing part 206 reflects part of the return light to the wavefront sensor 215, and the return light is used to measure the wavefront of the light beam.

The wavefront sensor 215 is connected to an adaptive optics control part 216 and transmits the received wavefront to the adaptive optics control part 216. The wavefront correction device 208 is also connected to the adaptive optics control part 216 and applies modulation instructed by the adaptive optics control part 216 to the measuring light or the return light. The adaptive optics control part 216 calculates an amount of modulation (amount of correction) to make a correction to obtain a wavefront without aberration based on the wavefront acquired from the measurement result of the wavefront sensor 215. The adaptive optics control part 216 further instructs the wavefront correction device 208 to provide the amount of modulation to the measuring light or the return light. The measurement of the wave front and the instruction to the wavefront correction device 308 are repeatedly performed, and feedback control is performed so that the wavefront of the return light is always optimal.

The light dividing part 204 reflects part of the reflected and scattered light transmitted through the light dividing part 206, and the reflected and scattered light is guided to a light intensity sensor 214 through a collimator 212 and an optical fiber 213. The light intensity sensor 214 converts the light into an electrical signal, and a control part 217 transmits the data to the image generating device 10 to form image data (moving images or still images).

The oscillation angle of the scanning optical system can be increased in the configuration of FIG. 2 to instruct the adaptive optics control part 216 not to correct the aberration, and the SLO image pickup device 20 can operate as a normal SLO device to image a wide-angle SLO image (WFSLO image). A device other than the SLO image pickup device 20 including the adaptive optics may take the wide-angle SLO image. The movement of the eye is followed (tracked) in some cases to reduce the influence of involuntary eye movement, eye movement due to poor fixation, or movement of the eye associated with movement of the head. An example of the measurement of the movement of fundus includes a method of measuring the movement of fundus by pattern matching, in which a fundus image generated by the image generating device is used, a calculation part not illustrated extracts a template image that is a small image with a character, and a region that most resembles the template image is searched. In the method, a scanner not illustrated can be installed in the optical system, and a control part not illustrated can be installed at a position connecting the scanner and the calculation part to cause the position of the emitted light to follow the movement of the fundus measured by the scanner. This can reduce the shift in the imaging position between the frames in one movie.

<Processing Procedure of Image Processing Device>

Figure 3:
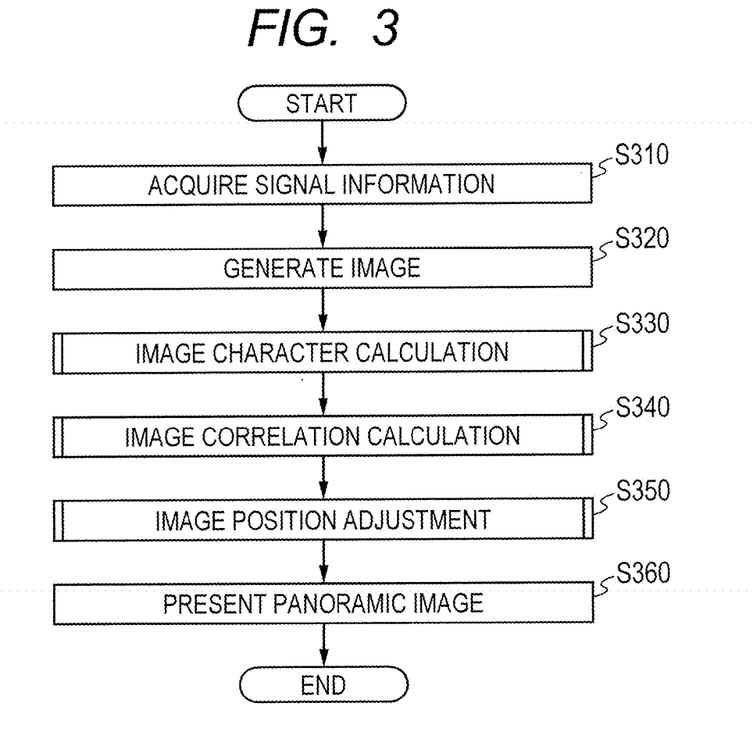
FIG. 3 is a flow chart illustrating a processing procedure of the image generating device according to the present invention.

A processing procedure of the image generating device 10 of the present embodiment will be described with reference to a flow chart of FIG. 3.

<Step S310>

In step S310, the signal acquiring part 100 acquires signal information of a plurality of images or moving images acquired from the adaptive optics SLO device connected to the image generating device 10. The signal information includes position signals of the galvano scanners or the resonant scanner used to image the retina and includes reflected signals from the retina acquired by imaging. The acquired signal information is stored in the memory part 130 through the control part 120.

In this case, control information of hardware attached to the acquired signal information is acquired and stored in the memory part 130 through the control part 120. The control information here includes the sampling frequency in acquiring the reflected signals of retina and the frame rate equivalent to the frequency of the galvano scanners. The control information may be written in an imaging information file attached to the signal information or may be included as tag information of the signal information.

<Step S320>

In step S320, the image generating part 140 generates images or moving images from the signal information acquired by the adaptive optics SLO device stored in the memory part 130. More specifically, the image generating part 140 generates WFSLO images and images (AOSLO images) with corrected aberration at a smaller field angle than the WFSLO images. The acquired images or moving images are stored in the memory part 130 through the control part 120. Although the acquired images or moving images have a general rectangular shape in the present embodiment, the shape is not limited to this.

<Step S330>

In step S330, she image character calculation part 151 calculates character amounts of character area in the images or moving images acquired in step S320. The calculated character amounts are stored in the memory part 130 through the control part 120. Therefore, the image character calculation part 151 functions as a second calculation unit that calculates character amounts of a plurality of images in the present embodiment.

Figure 4:
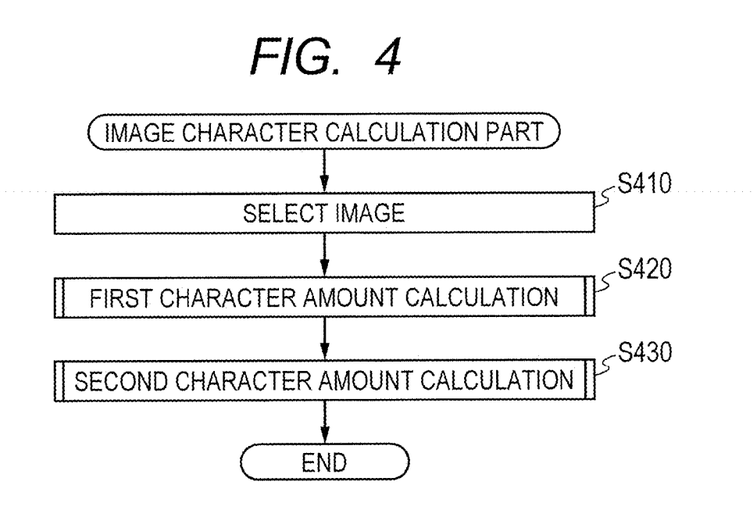
FIG. 4 is a flow chart describing in detail a step of calculating image characters in the flow chart illustrated in FIG. 3.

FIG. 4 illustrates a flow chart for describing details of the calculation of the image character amounts (step S330). In fundus grayscale images as in the present embodiment, blood vessels and lesions, such as edema and bleeding parts, often extend over a plurality of small-angle images. Therefore, the areas are handled as character areas in the present embodiment, and a first character amount is calculated from the character areas. If there is a large structural object extending over a plurality of images, the structural object may be handled as a character area for calculating the first character amount.

In addition, a structural object with a large difference from surrounding pixels that is not so large as to extend over a plurality of images is handled as a second character area, and a second character amount is calculated from the second character area. In the present embodiment, photoreceptor cells and small lesions are handled as the structural objects. However, the structural object for calculating the character amount is not limited to this.

If a sufficient result can be obtained by calculating only one of the first character amount and the second character amount, only one of the character amounts may be calculated to reduce the amount of calculation. The method of calculating the character amounts is not limited to the target and the method written here, and any type of structural object in the image can be used as long as the image position adjustment can be performed. Character amounts other than the two character amounts described above may also be used.

<Step S410>

In step S410, the image character calculation part 151 selects at least one of the images or moving images acquired in step S320 that is to be used to calculate the character amounts. For example, the image character calculation part 151 selects all WFSLO images acquired in step S320. The brightness of images may be acquired in advance in selecting the WFSLO images, and the images may not be selected if the brightness is equal to or lower than a predetermined value. Sufficient character amounts may not be detected in steps S420 and S430 described later from images with the brightness equal to or lower than the predetermined value, and an unnecessary process can be eliminated by not selecting the images with the brightness equal to or lower than the predetermined value. AOSLO images may be selected in addition to the WFSLO images, or only AOSLO images may be selected.

In the case of moving images, an image in at least one movie with the largest character amount calculated in steps S420 and S430 described later may be selected. Here, only one of them may be selected, or one of them may be prioritized and selected. Position adjustment between images of the frames in at least one movie may be performed, and frames with extremely low brightness due to blinking, frames with image distortion due to involuntary eye movement and frames with low S/N ratio due to poor aberration correction may be handled as exceptional frames. The exceptional frames may be removed, and remaining images may be used to generate and use an averaged image.

An arbitrary well-known position adjustment method can be used for the method of position adjustment between frames and acquisition of averaged image. If images with the same visual fixation are images at relatively the same position when the visual fixation of the examined eye is excellent, one of the methods may be used for a plurality of moving images at the same position to select at least one of the images. The user may select an image, or the averaged image may be manually created and used.

Steps S420 and S430 may be skipped for images with the field angle equal to or greater than a predetermined value. For example, when the WFSLO images are selected in step S410, steps S420 and S430 may be skipped.

<Step S420>

Figure 7:
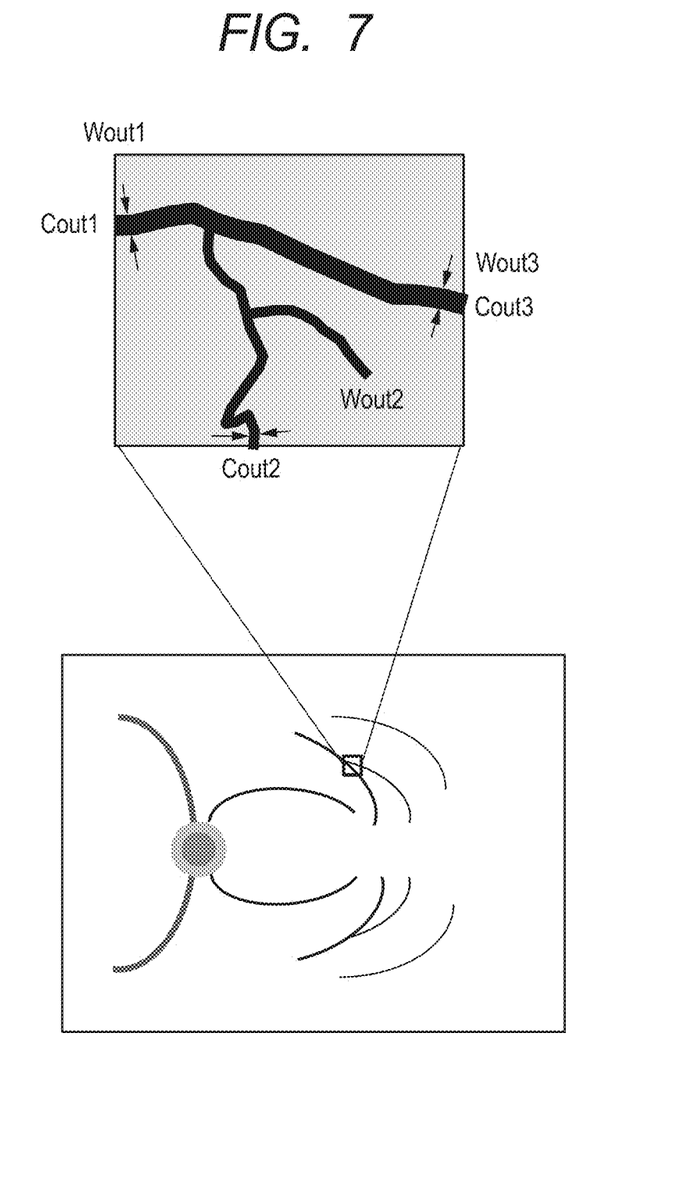
FIG. 7 is a diagram describing a step of calculating a first character amount in the flow chart illustrated in FIG. 4.

In step S420, the image character calculation part 151 calculates the first character amounts of at least one or more images selected in step S410. FIG. 7 presents an example of an image in which the first character amount is calculated based on blood vessels. The lower part of FIG. 7 illustrates an image of fundus with a wide field angle, wherein a papilla is on the left side, and arcade vessels extending rightward can be seen from the upper side to the lower side in the image. The upper part of FIG. 7 illustrates an image with a small field angle, imaging above a thick blood vessel near the arcade vessels surrounded by a rectangle on the wide-angle image. In this step, an average brightness value Ai and a blood vessel area Vi in each image are first acquired.

An arbitrary well-known blood vessel extraction method can be used as the method of acquiring the blood vessel area. In the present embodiment, the blood vessel area is an area with the brightness value equal to or lower than a threshold T1, which is an area with a dark color in the image of FIG. 7. Points of intersection of image ends of a sequence of points obtained by thinning the blood vessel area Vi and frame borders defining the surrounding of the image are acquired as Coutn (n=1, . . . , n2). In the present embodiment, there are three points of Coutn. The widths Woutn (n=1, . . . , n2) of the blood vessels near the intersecting points are also acquired, A blood vessel with a thicker diameter often extends long, and this index is also used because the blood vessel may extend over a plurality of images. These Coutn and Woutn correspond to the first character amount.

Although not illustrated, edema or a bleeding part with a characteristic structure that is a lesion of fundus may be the target. For example, if the brightness of these areas is low, the character amount is calculated by the same method. If the brightness is high, only areas larger than spots of photoreceptor cells are detected from the areas equal to or greater than a threshold T2, and an arbitrary well-known edge extraction method is used to similarly acquire the number of surfaces intersecting with the image ends and the widths of the surfaces. Although the method described above is used for the images of retina, large structural objects suitable for the images may be the targets in the case of other images. Even for RGB images, an arbitrary well-known segmentation method can be used to calculate the number of surfaces where the structural object is in contact with the image ends, as well as the widths of the surfaces.

<Step S430>

In step S430, the image character calculation part 151 calculates the second character amounts of at least one or more images selected in step S410. The structural object other than the area Vi that is a large structural object detected in step S420 is detected as a second character area for detecting the second character amount. For example, the photoreceptor cells are not distinctly observed in the blood vessel or the lesion that is the area Vi, and the targets of the calculation of the second character amount are the photoreceptor cells in the image of retina.

Figure 8:
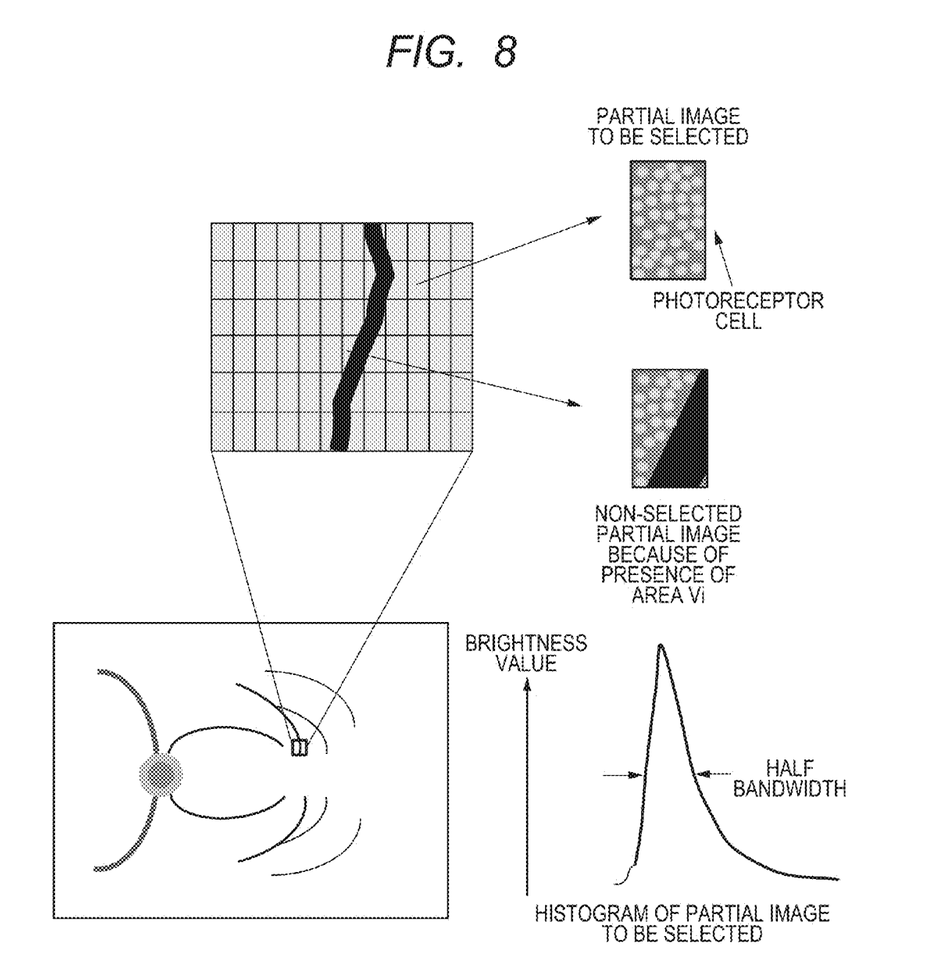
FIG. 8 is a diagram describing a step of calculating a second character amount in the flow chart illustrated in FIG. 4.

FIG. 8 presents a diagram describing a method of calculating the second character amount in the photoreceptor cells. The lower part of FIG. 8 illustrates an image of fundus with a wide field angle, and the upper part of FIG. 8 illustrates an image with a small field angle, imaging above one blood vessel. Only photoreceptor cells may be imaged in an image with a small field angle not actually including a capillary vessel. Consequently, the photoreceptor cells are not distinctly imaged depending on the focus, and the number of characters is significantly small. This is calculated as a character amount. Therefore, the second character amount is calculated and analyzed in an area other than the blood vessels or the lesions used for the first character amount. Although FIGS. 7 and 8 use different images for the description, steps S420 and S430 are sequentially executed for the same image.

Here, the image is divided into a plurality of parts as in FIG. 8, and a plurality of partial areas not including the blood vessel area Vi (including the lesion) detected in step S420 are selected. A histogram of brightness values of the plurality of selected partial images is created, and the half bandwidth is calculated to acquire the half bandwidth of a partial image with a large half bandwidth. A large image half bandwidth of the histogram indicates that the distribution of the pixel values is wide. When only fluorescence spots with high brightness, such as photoreceptor cells, exist in the image, this may be indicating the sharpness of the image. The half bandwidth may be acquired by an arbitrary well-known method, such as by performing Gaussian fitting to calculate the half bandwidth.

When there are a plurality of peaks of the histogram, the half bandwidths may be obtained for the plurality of peaks, and the sum of the half bandwidths may be acquired as the half bandwidth of the image. In addition, the sharpness of the shape of the small structural object, i.e., degree of distinct existence of a characteristic shape, may be evaluated by an arbitrary well-known photoreceptor cell count method, such as a method of scaling the density of the photoreceptor cells and the feeling of sharpness of the fluorescence spot of one photoreceptor cell.

As described, the image character calculation part 151 can calculate the character amount of a large structural object extending over a plurality of images, or more specifically, can calculate, as the character amount, the number of parts where the structural object and the image ends intersect, the size, or the area in the image of the structural object. Alternatively, the sharpness of the structural object in the image can be calculated as the character amount.

<Step S340>

In step S340, the image correlation calculation part 152 calculates, as a degree of correlation for example, correlation information between the images selected in step S410 among the images acquired in step S320. The information of the calculated correlation between the images is stored in the memory part 130 through the control part 120. In the present embodiment, the image correlation calculation part 152 functions as a calculation unit that calculates the degree of correlation between a plurality of images.

Figure 5:
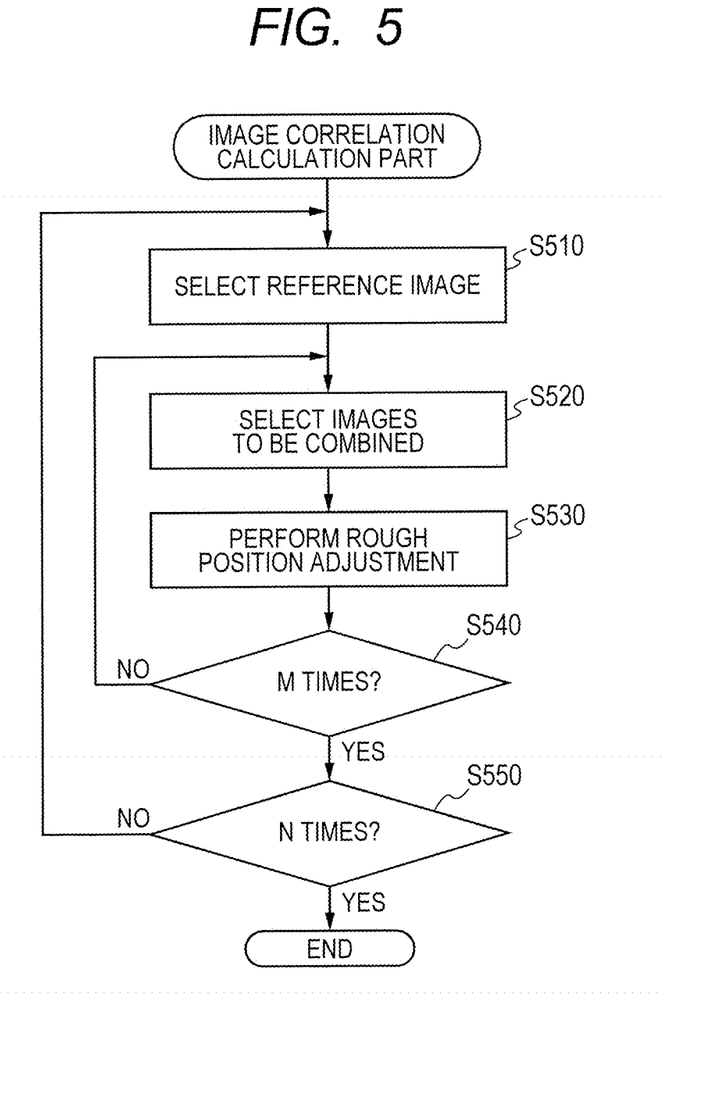
FIG. 5 is a flow chart describing in detail a step of calculating an image correlation degree in the flow chart illustrated in FIG. 3.

FIG. 5 illustrates a flow chart for describing details of the calculation of the correlation of the images (step S340). The degrees of correlation between images of at least two or more combinations are calculated to evaluate the relationship between the images.

<Step S510>

In step S510, the image correlation calculation part 152 selects at least one of the images acquired in step S410. All of the images acquired in step S410 may be selected, or only WFSLO images may be selected. Only AOSLO images may be selected.

If all images have the same field angle, the degrees of correlation of all or a plurality of combinations are calculated. Therefore, any images can be selected. Only an image with a large character amount among the images selected in step S410 may be selected as a reference image. When images with a plurality of field angles are included, more degrees of correlation of images may be calculated if an image with the maximum field angle is selected first. Only an image designated by the user may be selected.

<Step S520>

In step S520, the image correlation calculation part 152 selects at least one of the other images as an image to be combined, with respect to the reference image selected in step S510. Any image may be selected if all images have the same field angle. When images with a plurality of field angles are included, the amount of calculation can be reduced by selecting images with the same field angle or with close field angles. However, the selection method is not limited. The WFSLO images may be selected in step S510, and only images with the same field angle may be selected in step S520. Images with narrower field angles than the WFSLO images, such as AOSLO images, may be selected in step S520.

<Step S530>

In step S530, the image correlation calculation part 152 performs rough position adjustment of at least two images selected in steps S510 and S520, i.e., between at least two or more images. For an image in which the accuracy is not guaranteed although the position can be recognized on some level, such as when a fixation lamp is used for an examined eye with excellent visual fixation, the amount of calculation may be reduced if the predicted position is set as an initial position of the search. Therefore, the position adjustment may be performed based on information regarding the visual fixation associated with each image.

Here, a pattern matching method that is an arbitrary well-known method is used to calculate the degree of correlation between images to be combined with respect, to the reference image. In the present embodiment, a phase restriction correlation function is calculated to obtain a maximum correlation peak value as the degree of correlation and to obtain the coordinates at this time as the position of rough position adjustment. The degree of correlation and the position information of the rough position adjustment are stored in the memory part 130 through the control part 120.

In addition, similar pixel values may be used to use a general method of pattern matching, such as SAD (sum of absolute values of differences between brightness values), SSD (sum of squares of differences between brightness values) and normalized cross-correlation. If the correlation is low so that an overlapping area (overlap) is not found in the position adjustment using only two sets of images, the information indicative of unmatched images is stored in the memory part 130 through the control part 120. Therefore, any method, that can acquire information indicating the correlation between images can be used, and the method is not limited to the pattern matching.

As described, the image correlation calculation part 152 can use the phase restriction correlation function to calculate the position with the best correlation and the degree of correction between the images in the position adjustment between images. The position adjustment may be performed between images designated by the user, and the degree of correlation may then be calculated. Alternatively, the degree of correlation between combinations of at least a plurality of images can be calculated.

<Step S540>

In step S540, if the number of times that the position adjustment is performed for the images to be combined for which the degree of correlation is calculated in step S530 is M, the image correlation calculation part 152 advances to step S550A Although id corresponds to the number of combinations of all images with respect to the reference image in the present embodiment, M is not limited to this. If the number of times that the position adjustment is performed for the images to be combined for which the degree of correlation is calculated in step S530 is smaller than M, the process returns to step S520, and an image to be combined for which the position adjustment is not performed yet is selected to repeat step S530.

<Step S550>

In step S550, whether the rough position adjustment is performed for all reference images is determined. It is assumed here that the number of reference images selected to calculate the degree of correlation in step S510 is N, The image correlation calculation part 152 calculates the degrees of correlation of all images to be combined acquired in steps S520 to 540, with respect to a reference image. If the number of times that the rough position adjustment is performed is N which is equal to the number of selected reference images, this step ends. Although N is the number of all reference images in the present embodiment, N is not limited to this. If the number of reference images for which the degree of correlation of all images to be combined acquired in steps S520 to S540 are calculated is smaller than N, the process returns to step S510, and a reference image for which the calculation is not performed yet is selected to repeat steps S520 to S540.

<Step S350>

In step S350, the position adjustment part 153 sequentially performs image position adjustment and image stitching based on the character amounts of the images and the correlation information between the images acquired in steps S330 and S340. The position information of the images for which the position adjustment is performed and the panoramic image are stored in the memory part 130 through the control part 120. Therefore, in the present embodiment, the position adjustment part 153 functions as an order determination unit that determines the order of the position adjustment of a plurality images for generating a panoramic image by attaching the plurality of images based on the calculation results of the image character calculation part 151 and the image correlation calculation part 152.

Figure 6:
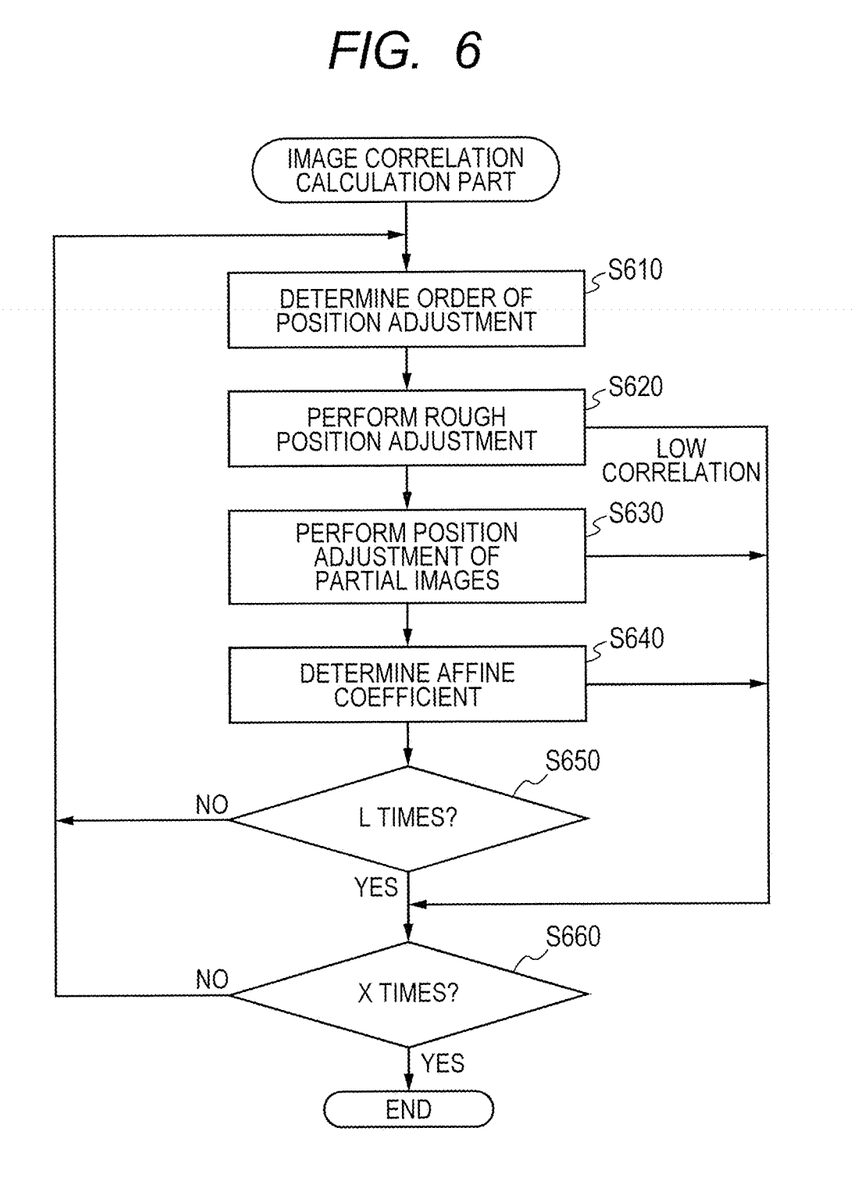
FIG. 6 is a flow chart describing in detail a step of image position adjustment in the flow chart illustrated in FIG. 3.

FIG. 6 illustrates a flow chart for describing details of the image position adjustment (step S350). The position adjustment is sequentially performed for the images, and the position information is stored in the memory part 130 through the control part 120.

<Step S610>

In step S610, the position adjustment part 153 determines the order of position adjustment based on the character amounts of the images and the correlation information between the images acquired in steps S330 and S340. A method, of determining the order when all images have the same field angle will be described, below in the present embodiment.

First, a reference frame that serves as a reference of position adjustment is determined. In a reference frame selection method, an image satisfying the following three conditions is selected as a reference frame: (1) images included a lot in a combination with a large degree of correlation calculated in step S530; (2) the number of Coutn calculated in step S420 is large, and the average value of Woutn is large; and (3) the half bandwidth of the histogram calculated in step S430 is wide. The number of conditions for selecting the reference frame may be less than three or four or more. The condition (1) may be a condition that the images have a large sum of the degrees of correlation with respect to the other images. A fixed threshold serving as a reference for determining whether the value is large in the conditions may be set, or a variable threshold may be set so that the value is relatively large in the acquired image.

In the present embodiment, highly related images with a large character extending over a plurality of images and with high sharpness can be selected. Therefore, the priorities are (1), (2) and (3) in selecting the reference frame. However, the priorities are not limited to these, and the user may select the images. The conditions (1) to (3) may be weighted, and all conditions may be taken into account to select the reference frame. The reference frame may be selected based only on one of the conditions (1) to (3). For example, an image with the highest sum of degrees of correlation with the other images may serve as the reference frame.

Subsequently, an image for which the position adjustment will be performed next is selected. First, images in which the first character amount calculated in step S420 is greater than a predetermined value are selected from images in which the degree of correlation is greater than a predetermined value with respect to the selected reference frame. Furthermore, images in which the second character amount is greater than a predetermined value is selected from the selected images. As a basis for selecting the next image, an image corresponding to the priorities (1), (2) and (3) is similarly selected in the present embodiment. The position adjustment of the sequentially selected images is performed with respect to the panoramic image generated by using the reference frame and the images for which the position adjustment is performed so far. Therefore, the condition used in (1) is a sum of the images correlated to both of the reference frame and the images for which the position adjustment is performed so far. When the determination of the position adjustment sequence is advanced, there may be no image with the degree of correlation greater than the predetermined value with respect to the panoramic image. Therefore, the threshold may be decreased according to the determination situation of the position adjustment sequence. When there is no image with the degree of correlation equal to or greater than the predetermined value, an image with the highest correlation with respect to the panoramic image may be selected from the remaining images.

When the position adjustment is performed only with the WFSLO images for example, a process of selecting, as a reference frame, an image with the highest correlation with respect to the other WFSLO images and performing the position adjustment of an image with the next highest correlation with respect to the other WFSLO images is repeated. In this way, even for the AOSLO images, only the condition (1) may be used to determine the position adjustment sequence.

In another selection method, an image in which the position calculated with respect to the reference frame in step S530 is distant may be preferentially selected, for example. This is to create a panorama as large as possible at every position adjustment in order to perform the position adjustment in a wide range. An image at a matched position near a blood vessel with large Wout may be preferentially selected, and the selection method of image is not limited to these. Although the order of all images may be determined at the beginning, the order may be sequentially determined for each image. For the reference frame or the order between some images, an image or order designated by the user may be selected. As described, a module area that functions as an order determination unit can use at least one or more types of character amounts in random order regarding the plurality of types of character amounts calculated by the image character calculation part 151.

When images with a plurality of field angles are included, more images with high degrees of correlation can be selected, if the field angle is maximum first. When images are sequentially selected, the images may be selected in descending order of field angle. The images may be selected in random order of field angle or may be selected in order of closer field angles between previous and next images. The method of selecting images is not limited to these, and determining the order of position adjustment of all or some images is a characteristic of the present invention.

Figure 10:
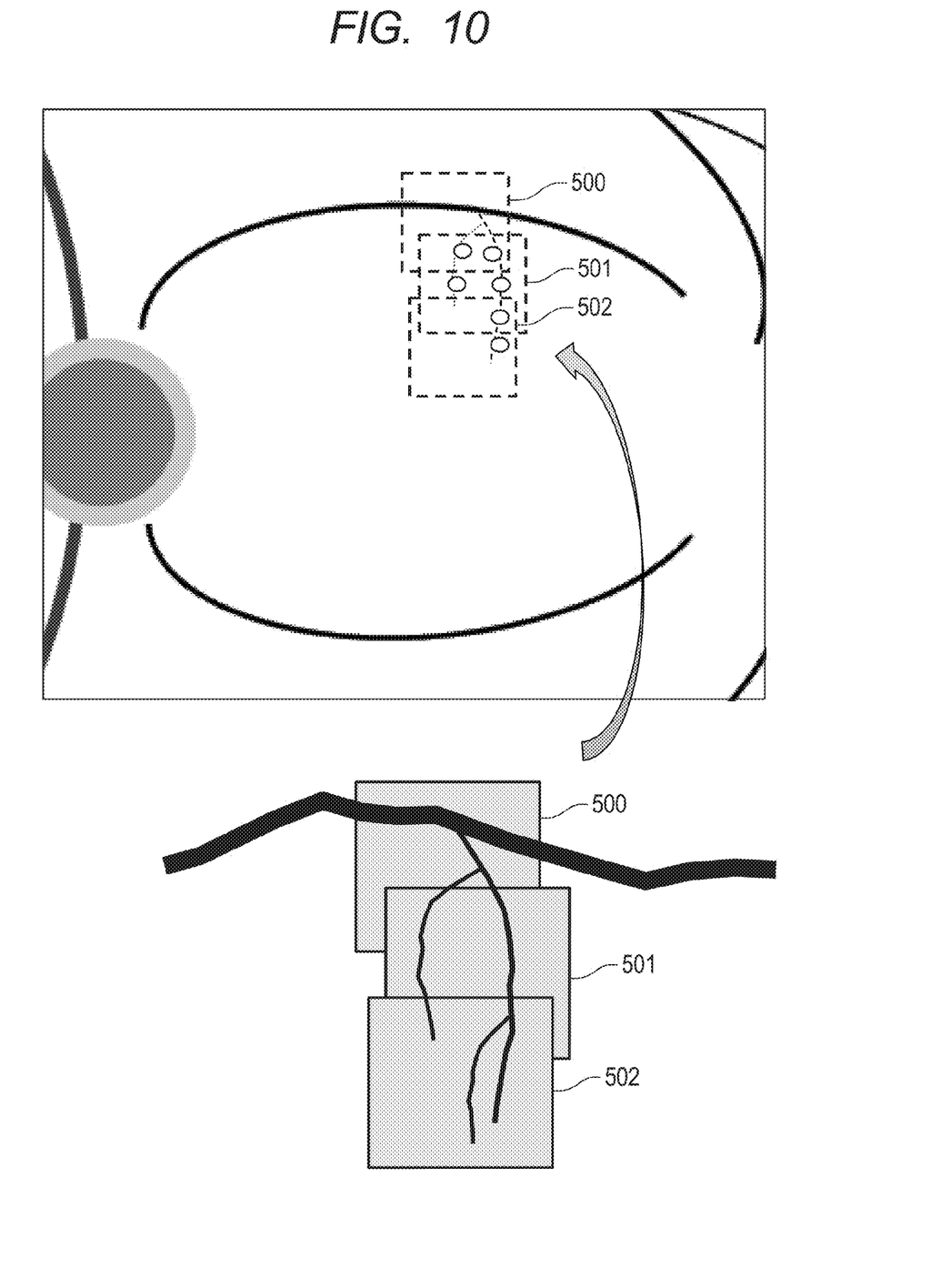
FIG. 10 is a diagram describing an example of a position adjustment sequence of the present invention.

For example, a determination method of the position adjustment sequence will be described with reference to FIG. 10. FIG. 10 illustrates a state in which position adjustment of three AOSLO images is performed on a WFSLO image. Images with different field angles are included, and the WFSLO image is first selected as a reference frame as described above. In FIG. 10, character parts, such as blood vessels, are unclear in an AOSLO image 501. In the drawing on the upper part of FIG. 10, dotted lines illustrate blood vessels.

The degree of correlation of an AOSLO image 500 including a large blood vessel is higher than the degrees of correlation of AOSLO images 501 and 502 with respect to the WFSLO image. The AOSLO image 502 is clearer than the AOSLO image 501, and the degree of correlation is high with respect to the WFSLO image. Therefore, the position adjustment is performed in the order of the AOSLO image 500, the AOSLO image 502 and the AOSLO image 501, which is the descending order of the degree of correlation with respect to the WFSLO image. In this way, the position adjustment of the AOSLO image 501, in which the position adjustment is difficult because the degree of correlation is low with respect to the WFSLO image, can be performed based on the character parts of the AOSLO images 500 and 502. Compared to when the position adjustment of the AOSLO image 501 is performed after the position adjustment of the AOSLO image 500 relative to the WFSLO image, the accuracy of the position adjustment can be improved to prevent failures, because the AOSLO image 502 can also be used as a reference of the position adjustment. The AOSLO images in the lower part of FIG. 10 are enlargement of the AOSLO images in the upper part. Although the blood vessels of the AOSLO image 501 in the lower part of FIG. 10 are clearly illustrated to indicate that the position adjustment is performed, the blood vessels are actually unclear as described above.

<Step S620>

In step S620, the position adjustment part 153 performs rough position adjustment of an image selected next for which the position adjustment will be performed, with respect to the reference frame selected in step S610 or the panoramic image for which the position adjustment is performed so far. In the present embodiment, the position calculated in step S530 is the initial position of the search. Although the calculation can be performed faster if the search range is limited on some level, the entire search range may be searched. The method of the rough position adjustment is the same as in step S530, and the position information of the rough, position adjustment is stored in the memory part 130 through the control part 120. If the correlation is relatively low here, the image may be stored in the memory part 130 as an unmatched image through the control part 120, and the process may proceed to step S660.

<Step S630>

In step S630, the position adjustment part 153 performs position adjustment based on each small image obtained by dividing the selected image, with respect to the reference frame selected in step S610 or the panoramic image for which the position adjustment is performed so far. The division of the image can be determined based on the character of the image. Although the image is divided 12×12 in the present embodiment, the number is not limited to this.

The method of performing the position adjustment of each small image with respect to the reference frame or the panoramic image for which the position adjustment is performed so far is an arbitrary well-known method, in which the position of the rough position adjustment that is set in step S620 serves as the initial position. In the present embodiment, the phase restriction correlation function is calculated as in step S620, and the position with the highest correlation peak value of each small image is acquired.

If there are many images with relatively low correlation, the images may be stored in the memory part 130 as unmatched images through the control part 120, and the process may proceed to step S660.

<Step S640>

In step S640, the position adjustment part 153 uses an arbitrary well-known method to determine an affine coefficient of the images to be combined based on the positions of the small images obtained by dividing the images to be combined for which the position adjustment is performed, acquired in step S630, with respect to the reference frame or the panoramic image for which the position adjustment is performed so far. In the present embodiment, a dot group Si obtained by arranging the center positions of the small images on a plane surface is first created based on the positions acquired in step S630. The center positions of the small field angles for which only the division is performed at the initial stage of the images to be combined, serve as a dot group Ai.

The least squares method is used to change the affine coefficient to minimize the sum of the distances between the coordinates of the dot group Ai corresponding to the same positions of the small field angles of the dot group Si. The affine coefficient when the sum of the distances is the smallest is acquired and set as position information. The images changed by this affine deformation are attached to the reference frame or the panoramic image for which the position adjustment is performed so far. The attached images are stored in the memory part 130 through the control part 120.

The module area that functions as an arithmetic unit in the position adjustment part 153 of the present embodiment calculates the shift amount of each image described above. The position adjustment part 153 also includes a module area that functions as a stitching unit. The stitching unit deforms the images based on the shift amounts calculated by the arithmetic unit and stitches the images after the deformation according to the order determined by the order determination unit to generate a panoramic image. As described, the module area that functions as the arithmetic unit can use the phase restriction correlation function between images to calculate the shift amounts.

The stitched images are used for the position adjustment of the next image, and the stitched images are updated at each position adjustment. The method of stitching and combining may be an arbitrary well-known method, and for example, blending may be performed only at edge sections. More specifically, stitching can be performed by applying alpha blending to the end sections of the images. Alternatively, in stitching the images, the brightness value may be adjusted to adjust the brightness of each image.

In the stitching, the character amount, such as the number of Coutn calculated in step S420, the average value of Woutn or the half bandwidth of the histogram calculated in step S430, may be compared with the character amount of the reference frame or the panoramic image for which the position adjustment is performed so far. An image with a higher character amount may be selected as an upper image. The user may select which one of the images is to be placed above.

When the sum of the shift amounts is greater than some level or when many small field angles do not fail within the images to be combined after the deformation, the images can be set as unmatched images. In this case, the unmatched images may be stored in the memory part 130 through the control part 120, and the process may proceed to step S660. Although the simple deformation based on affine is handled in the present embodiment, other arbitrary well-known image conversion methods and correction methods may be used and performed. For example, optical distortion may be corrected, and the present embodiment is not limited to this method.

As described, the module area that functions as the arithmetic unit in this case can divide one of the images into small field angles to perform, the position adjustment of each. Alternatively, the phase restriction correlation function can be used to calculate the shift amount used in the position adjustment of the divided small field angles. Furthermore, one of the images can be divided into small field angles to perform the position adjustment of each, and then the affine conversion coefficient of each image of the small field angles can be acquired.

<Step S650>

In step S650, if the number of images for which the position adjustment is performed is L, the position adjustment part 153 proceeds to step S660. Although L is the number of all images in the present embodiment, L is not limited to this. If the number of images for which the position adjustment is performed, is less than L in step S650, the process returns to step S610. An image for which the position adjustment will be performed next is selected, and steps S610 to S640 are repeated. The process may return to S620 if the order of position adjustment is determined in advance.

<Step S660>

In step S660, after the position adjustment of all images acquired from steps S610 to S650 is finished, the position adjustment part 153 repeats steps S610 to S640 for images that did not match in steps S620 to S640 and performs the position adjustment again. The number of unmatched error images is multiplied by the number of times that the position adjustment is to be performed again, and the obtained number is defined as X. The process returns to step S610, and the position adjustment is performed again. The operation of the position adjustment may be repeated for a certain number of times until the position is not matched, and the number of times and whether to carry out the operation are not limited. The affine value of the image ultimately matched in the position adjustment and the ultimate panoramic image are stored in the memory part 130 through the control part 120. The unmatched image is handled as information of a mismatched image, and the image is not stitched to the panoramic image. Only the affine value of a position with the closest correlation is stored in the memory part 130 through the control part 120, When the position adjustment is carried out again, this step ends if the position adjustment is the set X-th time.

<Step S360>

In step S360, the output part 160 displays the panoramic image of retina stored in the memory part 130 in step S350, on a monitor through the output part 160. The parameters, such as the character amounts of the images and the correlation information between the images stored in the memory part 130 from steps S310 to S350, or the affine coefficients specifying the positions of the images are stored in a database. If there is designation by the user, only selected images may be stitched and output as a panoramic image again, or affine deformation of the mismatched images may be performed to stitch the images at positions with the highest correlations.

Figure 9:
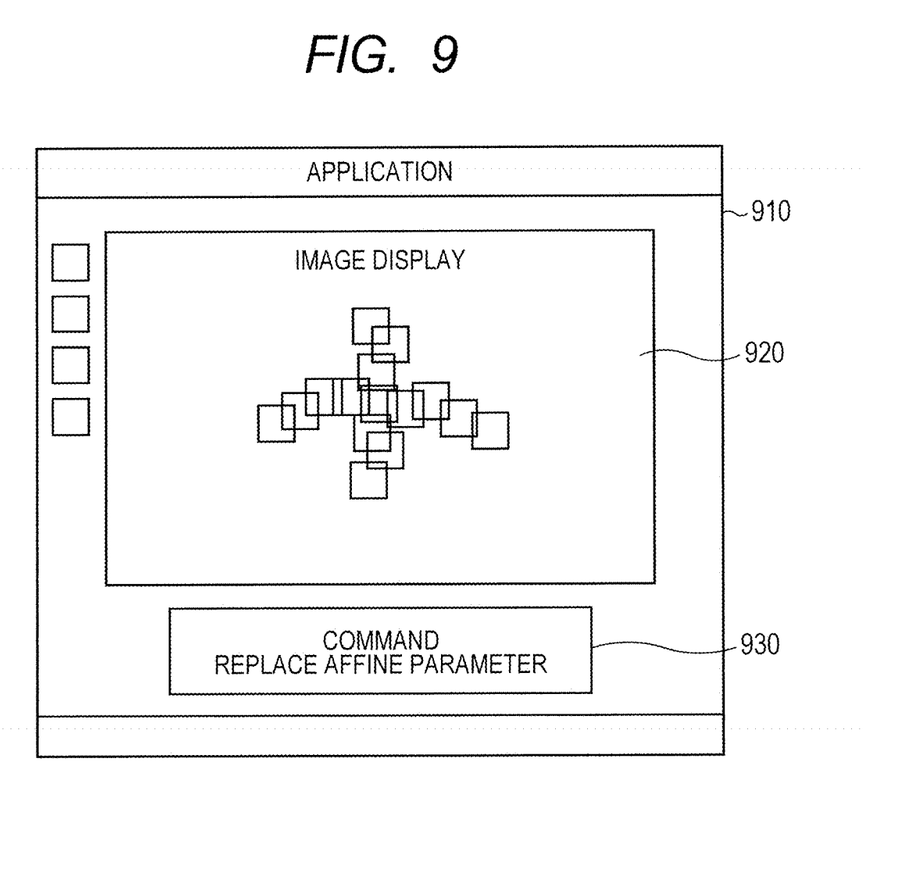
FIG. 9 is a diagram illustrating an example of a UI screen of a utility application according to the present Invention.

In addition, a utility application may be included, in which the mismatched images are arranged at an end on the monitor, and the user manually performs the position adjustment on the UI. FIG. 9 illustrates an example of a UI screen of the utility application. A main screen 910 displays a layer display part 920 of the generated panoramic image and an affine parameter replacement command window 930. In this example, the mismatched images are placed on the upper left of the application as described above, and a frame that allows display/non-display is indicated along with the images stitched on the panoramic image. The position adjustment of all images can be manually performed.

The manual position adjustment may be performed by an arbitrary well-known method, and parallel translation, rotation, scaling and shearing may be performed. The affine parameter replacement command window 930 can be used to directly adjust or collectively deform the parameters. The method is not limited to this as long as the position adjustment of the images can be manually performed in the utility application of the manual position adjustment.

As described, when an image group with few characters, such as high-definition images of fundus, in which accurate estimation of the information of imaging position is difficult, is stitched to generate a panoramic image, the order of position adjustment can be taken into account to reduce images for which the position adjustment cannot be accurately performed and to generate a panoramic image with few stitching failed images.

According to the configuration, images of retina acquired by an adaptive optics SLO device can be used to accurately perform position adjustment between images and to generate a panoramic image with few stitching failed images, without a special hardware configuration for specifying image positions.

Other Embodiments

The position adjustment of high-definition planar images of retina with few character amounts and small field angles is performed in the example described above. However, position adjustment between tomographic images of retina in a different modality, such as an OCT that is another high-resolution retina tomographic device, and position adjustment of one plane of a three-dimensional integrated image generated by integration of tomographic images of an OCT and planar images, such as AO-SLO of the present example, can be performed. The retina tomographic images here denote planar images in a depth direction perpendicular to a front image that are obtained by imaging the examined eye by a fundus camera from the front side. In this way, images of a plurality of modalities can be combined, and two-dimensional and three-dimensional position adjustments can be performed by similarly setting the order of position adjustment based on the character points unique to the images. Therefore, the imaging modality is not limited.

The present invention is not limited to the embodiments, and various deformations and changes can be made without departing from the scope of the present invention. For example, although the object to be measured is an eye in the embodiments, the present invention can also be applied to an object to be measured other than the eye, such as skin and organ. In this case, the present invention is in a form of medical equipment other than the ophthalmic device, such as an endoscope. Therefore, the present invention can be figured out as an examination device such as an ophthalmic device, and the examined eye can be figured out as a form of an object to be examined.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment (s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-106233, filed May 22, 2014, which is hereby incorporated by reference herein in its entirety.

What is claimed is:

1. An image generating device comprising:
   a first calculation unit configured to calculate degrees of correlation between a plurality of images;
   a second calculation unit configured to calculate an amount of character points in the plurality of images with respect to an image of a large structural object extending over the plurality of images; and an order determination unit configured to determine an order of performing position adjustment of the plurality of images for generating a panoramic image generated by stitching the plurality of images based on calculation results of the first calculation unit and the second calculation unit.

2. The image generating device according to claim 1, further comprising:
an arithmetic unit configured to calculate a shift amount of each of the images; and
a stitching unit configured to deform each of the images based on the shift amount calculated by the arithmetic unit and to stitch the images after the deformation according to the order determined by the order determination unit to generate the panoramic image.

3. The image generating device according to claim 1, wherein the second calculation unit calculates, as the amount of character points, a number of parts where the image of the large structural object extending over the plurality of images intersects with ends of the images.

4. The image generating device according to claim 1, wherein the second calculation unit calculates, for the character points, sizes of the parts where the image of the large structural object extending over the plurality of images intersects with the ends of the images.

5. The image generating device according to claim 1, wherein the second calculation unit calculates the amount of character points based on areas of the image of the large structural object extending over the plurality of images.

6. The image generating device according to claim 1, wherein the second calculation unit calculates, for the character points, sharpness of the image of the structural object in the plurality of images.

7. The image generating device according to claim 1, wherein the first calculation unit is adapted to perform position adjustment between at least two or more images.

8. The image generating device according to claim 1, wherein in the position adjustment between the images, the first calculation unit uses a phase restriction correlation function to calculate a position with a best degree of correlation between the images and the degree of correlation.

9. The image generating device according to claim 1, wherein the first calculation unit performs the position adjustment between the images designated by a user to calculate the degree of correlation.

10. The image generating device according to claim 1, wherein in the position adjustment between the images, the first calculation unit calculates the degree of correlation between combinations of some of the plurality of images.

11. The image generating device according to claim 1, wherein the order determination unit uses at least one or more types of character points in random order among a plurality of types of character points calculated by the second calculation unit.

12. The image generating device according to claim 2, wherein the arithmetic unit uses a phase restriction correlation function between the images to calculate the shift amount.

13. The image generating device according to claim 2, wherein the arithmetic unit divides the images into small images to perform the position adjustment of each of the small images.

14. The image generating device according to claim 2, wherein the arithmetic unit uses a phase restriction correlation function to calculate the shift amount used in the position adjustment of the divided small images.

15. The image generating device according to claim 13, wherein the arithmetic unit acquires an affine conversion coefficient of each of the images with the small field angles after dividing one of the images into small images and performing the position adjustment of each of the small images.

16. The image generating device according to claim 1, further comprising a stitching unit adapted to stitch the plurality of images, wherein the stitching unit is adapted to perform the stitching by performing alpha blending of end sections of each of the images.

17. The image generating device according to claim 1, further comprising a stitching unit adapted to stitch the plurality of images, wherein the stitching unit is adapted to perform brightness adjustment of each of the images in the stitching of the images.

18. The image generating device according to claim 1, wherein the panoramic image is an image of an examined eye.

19. The image generating device according to claim 18, wherein the image of the examined eye is an image in which aberration caused by the examined eye is corrected.

20. A non-transitory tangible medium having recorded thereon a program for causing a computer to realize the image generating device according to claim 1.

21. An image generating method comprising:
calculating degrees of correlation between a plurality of images;
calculating an amount of character points in the plurality of images with respect to an image of a large structural object extending over the plurality of images; and
determining an order of performing position adjustment of the plurality of images for generating a panoramic image generated by stitching the plurality of images based on the calculated degrees of correlation and number of character points.

* * * * *